(12) United States Patent
Pacetti

(10) Patent No.: US 8,530,526 B2
(45) Date of Patent: Sep. 10, 2013

(54) BIOBENEFICIAL COATING COMPOSITIONS AND METHODS OF MAKING AND USING THEREOF

(75) Inventor: Stephen D. Pacetti, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 346 days.

(21) Appl. No.: 12/874,892

(22) Filed: Sep. 2, 2010

(65) Prior Publication Data

US 2010/0330145 A1     Dec. 30, 2010

Related U.S. Application Data

(62) Division of application No. 10/723,043, filed on Nov. 26, 2003, now Pat. No. 7,807,722.

(51) Int. Cl.
*A61K 47/00* (2006.01)
*A01N 25/00* (2006.01)
*A61F 13/00* (2006.01)

(52) U.S. Cl.
USPC ............ 514/772.1; 514/772; 514/772.4; 424/422; 424/78.08; 424/78.17; 424/78.18; 424/78.31

(58) Field of Classification Search
None
See application file for complete search history.

(56) References Cited

U.S. PATENT DOCUMENTS

| | | | |
|---|---|---|---|
| 5,543,158 A | 8/1996 | Gref et al. | |
| 5,869,127 A | 2/1999 | Zhong | |
| 6,099,562 A * | 8/2000 | Ding et al. | 623/1.46 |
| 6,099,563 A | 8/2000 | Zhong | |
| 6,179,817 B1 | 1/2001 | Zhong | |
| 6,197,051 B1 | 3/2001 | Zhong | |
| 6,231,590 B1 | 5/2001 | Slaikeu et al. | |
| 6,527,938 B2 | 3/2003 | Bales et al. | |
| 6,545,097 B2 | 4/2003 | Pinchuk et al. | |
| 6,835,387 B2 | 12/2004 | Herrmann | |
| 2002/0107330 A1* | 8/2002 | Pinchuk et al. | 525/242 |
| 2003/0236513 A1 | 12/2003 | Schwarz et al. | |

OTHER PUBLICATIONS

International Search Report and Written Opinion for application PCT/US04/39163, mailed Feb. 16, 2006, 9 pgs.

Büllesfeld et al., "Long-term evaluation of paclitaxel-coated stents for treatment of native coronary lesions", Zeitschrift fur Kardiologie vol. 92, No. 10 pp. 825-832 (2003).
Chao-Wei Hwang et al., "Physiological Transport Forces Govern Drug Distribution for Stent-Based Delivery", Circulation vol. 104, pp. 600-605 (2001).
Drachman et al., "Neointimal Thickening After Stent Delivery of Paclitaxel: Change in Composition and Arrest of Growth Over six Month", J. of the Am. College of Cardiology vol. 36, No. 7, pp. 2325-2332 (2000).
Grube et al., "Safety and Performance of a Pacilitaxel-Eluting Stent for the Treatment of In-Stent Restenosis: Preliminary Results of the Taxus III Trial", Abstracts, JACC ACCIS2002 (Angiography & Interventional Cardiology) pp. 58A-59A (2002).
Grube et al., "Six-and Twelve-Month Results from a Randomized, Double-Blind Trial on a Slow-Release Paclitaxel-Eluting Stent for De Novo Coronary Lesions", Circulation vol. 103, pp. 38-42 (2003).
Lambert et al., "Localized Arterial Wall Drug Delivery From a Polymer-Coated Removable Metallic Stent", Circulation vol. 90, No. 2, pp. 1003-1011 (1994).
Lincoff et al., "Sustained Local Delivery of Dexamethasone by a Novel Intravascular Eluting Stent to Prevent Restenosis in the Porcine Coronary Injury Model", JACC vol. 29, No. 4, pp. 808-816 (1997).
Pinchuk "A review of the biostability and carcinogenicity of polyurethanes in medicine and the new generation of 'biostable' polyurethanes", J. Biomater Sci. Polymer Edn. vol. 6, No. 3, pp. 225-267 (1994).
Pinchuk et al., "Polyisobutylene-Based Thermoplastic Elastomer for Ultra Long-Term Implant Applications", Soc. For Biomaterials, 1 pgs. (2000).
Tanabe et al., "In-Stent Restenosis Treated with Stent-Based Delivery of Paclitaxel Incorporated in a Slow-Release Polymer Formulation", Circulation 107; pp. 559-564 (2003).
Thymine, Material Safety Data Sheet Thymine MSDS, Science Lab. com, 6 pgs. (2008).
Van der Giessen et al., "Marked Inflammatory Sequelae to Implantation of Biodegradable and Nonbiodegradable Polymers in Porcine Coronary Arteries", Circulation vol. 94, No. 7, pp. 1690-1697 (1996).

* cited by examiner

*Primary Examiner* — Michael G Hartley
*Assistant Examiner* — Lance Rider
(74) *Attorney, Agent, or Firm* — Squire Sanders (US) LLP

(57) ABSTRACT

A biobeneficial coating composition for coating an implantable device, such as a drug eluting stent, a method of coating the device with the composition, and an implantable device coated with the composition are provided.

10 Claims, 2 Drawing Sheets

BIOBENEFICIAL COATING COMPOSITIONS AND METHODS OF MAKING AND USING THEREOF

CROSS REFERENCE TO RELATED APPLICATION

This application is a divisional application of U.S. application Ser. No. 10/723,043 filed on Nov. 26, 2003 now U.S. Pat. No. 7,807,722, the teaching of which is incorporated by reference herein in its entirety.

BACKGROUND OF THE INVENTION

1. Field of the Invention

This invention generally relates to a polymeric coating composition for coating an implantable device, such as a stent.

2. Description of the Background

Polymeric coatings have been used for coating stents. One of the commercially available polymer coated products is stents manufactured by Boston Scientific. For example, U.S. Pat. Nos. 5,869,127; 6,099,563; 6,179,817; and 6,197,051, assigned to Boston Scientific Corporation, describe various compositions for coating medical devices. These compositions provide to stents described therein an enhanced biocompatibility and may optionally include a bioactive agent. U.S. Pat. No. 6,231,590 to Scimed Life Systems, Inc., describes a coating composition which includes a bioactive agent, a collagenous material, or a collagenous coating optionally containing or coated with other bioactive agents.

The nature of the coating polymers plays an important role in defining the surface properties of a coating. For example, very a low $T_g$, amorphous coating material induces unacceptable rheological behavior upon mechanical perturbation such as crimping, balloon expansion, etc. On the other hand, a high $T_g$, or highly crystalline coating material introduces brittle fracture in the high strain areas of the stent pattern.

A current paradigm in biomaterials is the control of protein adsorption on the implant surface. Uncontrolled protein adsorption, leading to mixed layer of partially denatured proteins, is a hallmark of current biomaterials when implanted. Such a surface presents different cell binding sites from adsorbed plasma proteins such as fibrogen and immunoglobulin G. Platelets and inflammatory cells such as monocyte/macrophages and neutrophils adhere to these surfaces. Unfavorable events can be controlled by the use of non-fouling surfaces. These are materials, which absorb little or no protein, primarily due to their hydrophilic surface properties.

Another limitation of current drug eluting stents stems from the fact that the stent is a foreign body. Use of drug eluting stents has proved successful by use of controlled release of anti-proliferative drugs to control restenosis. However, drug eluting stents still have a small, but measurable, incidence of sub-acute thrombosis. Moreover, drug eluting stents have not driven restenosis to zero levels, especially in more challenging patient subsets such as diabetics or patients with small vessels, and/or long, diffuse lesions. A biomaterials-based strategy for further improving the outcome of drug eluting stents is by the use of biobeneficial materials or surfaces in stent coatings. A biobeneficial material is one which enhances the biocompatibility of a device by being non-fouling, hemocompatible, actively non-thrombogenic, or anti-inflammatory, all without depending on the release of a pharmaceutically active agent.

U.S. application No. 2002/0107330 to Pinchuk, et al., describes a composition containing a blend of polystyrene-polyisobutylene-polystyrene copolymer and paclitaxel in various ratios. The composition, when coated onto an implantable device, may be covered with a barrier layer of, or blended with, a polymer or material such as polyethylene oxide or hyaluronic acid (see also Pinchuk, et al., "Polyisobutylene-based Thermoplastic Elastomers for Ultra Long-Term Implant Applications," Society for Biomaterials, 6th World Biomaterials Congress Transactions, 2000, #1452; Drachman D E, et al., J. Amer. Coll Cardiology, 36(7):2325-2332 (2000); Pinchuk, J. Biomater. Sci. Polymer edn., 6(3):225-267 (1994)). However, it is well known in the art that many biobeneficial materials such as polyethylene oxide or hyaluronic acid are water-soluble and can be leached out of the composition such that the coating may lose biobeneficiality.

The present invention addresses such problems by providing a coating composition for coating implantable devices.

SUMMARY OF THE INVENTION

It is provided a biobeneficial composition for coating an implantable device or delivery of a bioactive agent. The biobeneficial composition comprises a first block copolymer and a biobeneficial polymer. Alternatively, the biobeneficial polymer may comprise a first block copolymer and a second block copolymer, the second block copolymer comprising a biobeneficial component and another component, which is either water soluble or miscible with the first block copolymer. The first block copolymer has a block with a $T_g$ below about body temperature and another block that has a $T_g$ above about body temperature or has considerable crystallinity with a $T_m$ above about body temperature. As used herein, the term "body temperature" refers to the normal body temperature of a human, which is about 37° C., e.g., about 36° C. to 37.5° C. The block with a Tg below about body temperature has an amorphous structure and is elastomeric. The composition described herein is elastomeric but very oxidation resistant. The high $T_g$ block renders the first block copolymer not very permeable, or accessible, to reactive oxygenated species. The elastomeric, low $T_g$ block can be oxidation resistant. The composition described herein may further include a bioactive agent.

The composition described herein can be used for coating an implantable device such as a stent or for controlled delivery of a bioactive agent.

DETAILED DESCRIPTION

Biobeneficial Compositions

Figure 1:
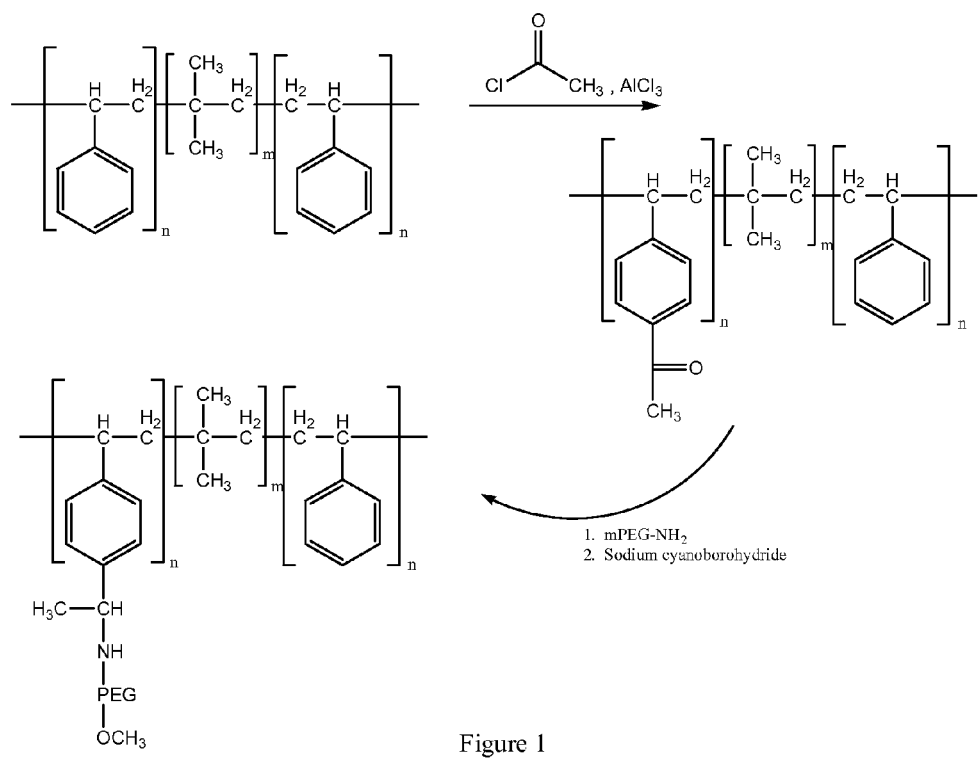
FIG. 1 is a scheme of forming a conjugate of polystyrene-polyisobutylene-polystyrene block copolymer with poly(ethylene glycol) (PEG).

A biobeneficial composition for coating an implantable device or delivery of a bioactive agent is provided. The biobeneficial composition comprises a first block copolymer and a biobeneficial polymer. Alternatively, the biobeneficial composition may comprise a first block copolymer and a second block copolymer, the second block copolymer comprising a biobeneficial component and another component that is either water insoluble or miscible with the first block copolymer. The first block copolymer has a block with a $T_g$ below about body temperature and another block with a $T_g$ above about body temperature or that has considerable crystallinity with a $T_m$ above about body temperature. The block with a $T_g$ below about body temperature has an amorphous structure and is elastomeric. Functionally, the elastomeric, low $T_g$ block provides for flexibility, and the block with $T_g$ or $T_m$ above about body temperature acts as a virtual crosslink. The composition described herein may further include a bioactive agent.

$T_g$ as used herein generally refers to the temperature at which the amorphous domains of a polymer change from a brittle vitreous state to a plastic state at atmospheric pressure. In other words, $T_g$ corresponds to the temperature where the onset of segmental motion in the chains of the polymer occurs, and it is discernible in a heat-capacity-versus-temperature graph for a polymer. When an amorphous or semicrystalline polymer is heated, its coefficient of expansion and heat capacity both increase as the temperature rises, indicating increased molecular motion. As the temperature rises, the sample's actual molecular volume remains constant. Therefore, a higher coefficient of expansion points to a free volume increase of the system and increased freedom of movement for the molecules. The increasing heat capacity corresponds to increasing heat dissipation through movement.

$T_g$ of a given polymer can be dependent on the heating rate and can be influenced by the thermal history of the polymer. Furthermore, polymer chemical structure heavily influences $T_g$ by affecting polymer mobility. Generally, flexible main-chain components lower $T_g$ and bulky side groups raise $T_g$. Similarly, increasing flexible-side-group length lowers $T_g$ and increasing main-chain polarity increases $T_g$. Additionally, the presence of crosslinks can increase the observed $T_g$ for a given polymer, and the presence of a drug or therapeutic agent can alter the $T_g$ of a polymer due to plasticization effects. The magnitude of these plasticization effects depends on the miscibility and compatibility of the drug and polymer and the loading of drug in the polymer.

As used herein, the term "biobeneficial" refers to an attribute of a material that increases the biocompatibility and/or bio-responses of a coating on an implantable device.

The term "water insoluble" as used herein refers to an attribute of a material having a quality of being insoluble as understood by one of ordinary skill in the art. One indication of a material's being insoluble is the material having a solubility in water less than or equal to 1% (w/w) or 10 mg/gm at 37° C. and 1 atm.

The composition described herein is elastomeric, but very oxidation resistant. The high $T_g$ block renders the first block copolymer not very permeable, or accessible, to reactive oxygenated species. The elastomeric, low $T_g$ block can be oxidation resistant. For example, the elastomeric, low $T_g$ block can be a polyisobutyl block, which is oxidation resistant because every other carbon is a tertiary carbon. Free radicals and oxidants can attach and oxidize the $CH_2$ moieties of the polyisobutyl block forming hydroxyl and carbonyl groups. However, due to the alternating secondary and tertiary carbons, no secondary carbons are adjacent, making it impossible to form carbon-carbon double bonds in the polymer backbone. Consequently, the backbone of the polyisobutyl block will remain intact.

The composition described herein can be used for coating an implantable device such as a stent or for controlled delivery of a bioactive agent. The composition can also be used to make an implantable medical device.

In accordance with one aspect of the invention, the composition disclosed herein comprises a conjugate of a first block copolymer comprising at least one elastomeric block having a $T_g$ below about body temperature and another block having a Tg or Tm above about body temperature with a biobeneficial polymer. The block having a $T_g$ above about body temperature has a structure of Formula I and the elastomeric block having a $T_g$ below about body temperature has a structure of Formula II:

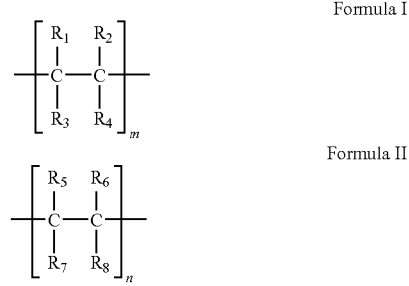

wherein $R_1$, $R_2$, $R_3$ and $R_4$ are independently hydrogen, phenyl, methyl, ethyl, carboxylate, acrylate, or methacrylate provided that $R_1$, $R_2$, $R_3$ and $R_4$ cannot be all hydrogen; $R_5$ and $R_7$ or $R_6$ and $R_8$ are independently methyl, ethyl, propyl, butyl, benzyl, or phenyl; and $R_6$ and $R_8$ or $R_5$ and $R_7$ are independently hydrogen, methyl, ethyl, propyl, benzyl, or phenyl. The high Tg block can be polystyrene, poly(methyl methacrylate), poly(ethyl methacrylate), poly(propyl methacrylate), poly(isopropyl methacrylate), poly(4-methylstyrene), poly(alpha-methyl styrene), poly(benzyl methacrylate), poly(tert-butyl methacrylate), poly(chloro-styrene), or poly(bromo-styrene). Useful elastomeric, low $T_g$ block includes, poly(isobutylene), poly(n-butyl methacrylate), poly (n-hexyl methacrylate), poly(n-octyl methacrylate), poly(n-lauryl methacrylate), poly(2-ethylhexyl methacrylate), and poly(octadecyl methacrylate). The first block copolymer can be an A-B diblock copolymer or A-B-A or B-A-B triblock copolymer.

In one embodiment, the first block copolymer has the following structure of formula III:

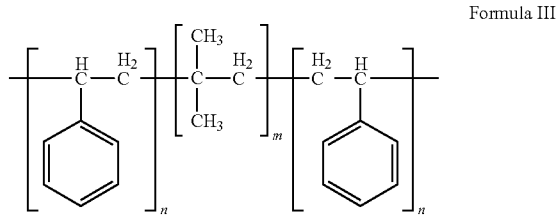

wherein m and n are positive integers.

In a further embodiment, the conjugate can have a structure of the following:

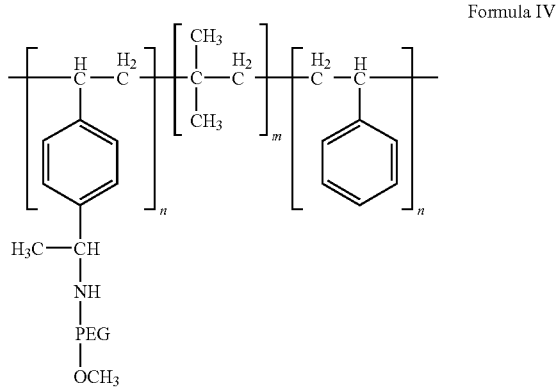

wherein m and n are positive integers; or

Formula V

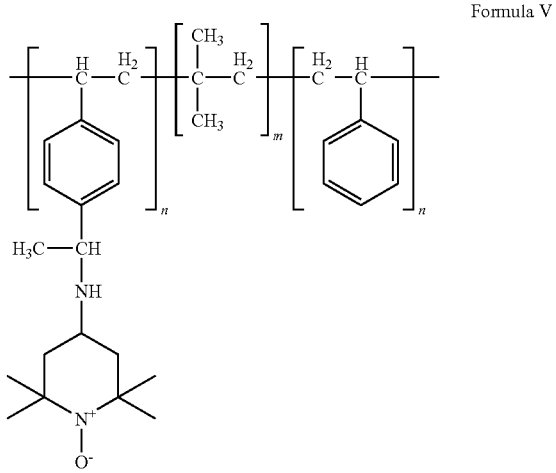

wherein m and n are positive integers.

Representative biobeneficial polymers include, but are not limited to, poly(ethylene glycol) (PEG), polypropylene glycol), PLURONIC™ surfactants which are block copolymers based on ethylene oxide and propylene oxide, poly(tetramethylene glycol), hydroxy functional poly(vinyl pyrrolidone), polyalkylene oxide, dextran, dextrin, sodium hyaluronate, hyaluronic acid, sulphonated poly(styrene), heparin, Elastin, Chitosan, poly(2-hydroxyethyl methacrylate), poly(3-hydroxypropyl methacrylamide), 4-amino-2,2',6,6'-tetrapiperidine oxide, stable nitroxides, super oxide dimutase mimics, free radical scavengers, and combination thereof. The biobeneficial can be conjugated to the high $T_g$ block of the block copolymer via a linkage, which can be a direct covalent bond, hydrogen bond, ionic bond or chelate. Preferably, the linkage is covalent such as through an amino linkage, an ester linkage, an ether linkage, a peptide linkage, an amide linkage, a urethane linkage, a carbonate linkage, via a carbon-carbon bond, a hydrazide linkage, a sulfonate linkage, a sulfone linkage, or a thiol ether linkage. The biobeneficial polymer can be attached to the high Tg block of the block copolymer via any method known in the art (see, for example, Michael Smith, Organic Synthesis, $2^{nd}$ Edition, McGraw-Hill, 2001).

As an example, PEG is attached to polystyrene-polyisobutylene-polystyrene (SIS) triblock copolymer via reductive amination as shown in FIG. 1. First, the SIS triblock copolymer is subjected to acylation in the presence of a Lewis acid catalyst such as $AlCl_3$. The acylated SIS triblock copolymer is then subjected to reductive amination with commercially available mPEG-$NH_2$ (available from vendors such as Nektar) in the presence of a reducing agent such as sodium cyanoborohydride, forming a SIS-PEG conjugate as shown in FIG. 1.

Figure 2:
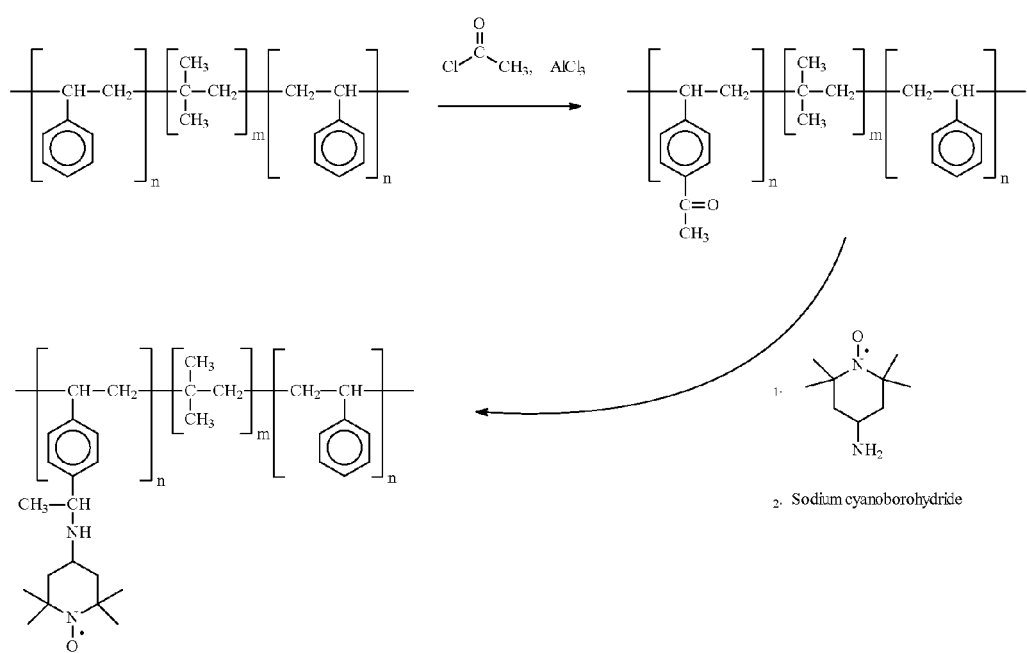
FIG. 2 is a scheme of forming a conjugate of polystyrene-polyisobutylene-polystyrene block copolymer with 4-amino-2,2,6,6-tetramethylpiperidine-1-oxide (4-amino-TEMPO).

As a further example, a small molecule such as 4-amino-2,2',6,6'-tetrapiperidine oxide (4-amino-TEMPO) can be attached to a SIS triblock copolymer as shown in FIG. 2. The SIS triblock copolymer is first subjected to acylation in the presence of a Lewis acid such as $AlCl_3$. The acylated SIS triblock copolymer is then subjected to reductive amination in the presence of sodium cyanoborohydride to form a 4-amino-TEMPO derivatized SIS triblock copolymer (FIG. 2).

In accordance with another aspect of the invention, the composition disclosed herein comprises a first block copolymer comprising a block with a $T_g$ above about body temperature and an elastomeric block with a $T_g$ below about body temperature and a second block copolymer comprising a biobeneficial component and another component which is water insoluble or miscible with the first block copolymer, which is described above. The component miscible with the first block copolymer is hydrophobic. Representative examples can include polystyrene-polyisobutylene-polystyrene block copolymer (SIS), polystyrene, polyisobutylene, polycaprolactone (PCL), poly(L-lactide), poly(D,L-lactide), poly(lactides), polylactic acid (PLA), poly(lactide-co-glycolide), poly(glycolide), polyalkylene, polyfluoroalkylene, polyhydroxyalkanoate, poly(3-hydroxybutyrate), poly(4-hydroxybutyrate), poly(3-hydroxyvalerate), poly(3-hydroxybutyrate-co-3-hydroxyvalerate), poly(3-hydroxyhexanoate), poly(4-hyroxyhexanoate), mid-chain polyhydroxyalkanoate, poly (trimethylene carbonate), poly (ortho ester), polyphosphazenes, poly (phosphoester), poly(tyrosine derivedarylates), poly(tyrosine derived carbonates). The water insoluble component of the second copolymer includes, for example, polydimethyloxanone (PDMS), polyvinylidene fluoride (PVDF), polyhexafluoropropylene (HFP), polydimethylsiloxane, poly (vinylidene fluoride-co-hexafluoropropylene) (PVDF-HFP), poly (vinylidene fluoride-co-chlorotrifluoroethylene) (PVDF-CTFE), poly(butyl methacrylate), poly(methyl methacrylate), poly(methacrylates), poly(vinyl acetate), poly(ethylene-co-vinyl acetate), poly(ethylene-co-vinyl alcohol), poly(ester urethanes), poly(ether-urethanes), poly(carbonate-urethanes), poly(silicone-urethanes), poly (urea-urethanes) and a combination thereof.

In one embodiment, the second block copolymer comprising a biobeneficial component is SIS-PEG, polystyrene-PEG, polyisobutylene-PEG, PCL-PEG, PLA-PEG, PMMA-PEG, PDMS-PEG, PVDF-PEG, SIS-hyaluronic acid (HA), polystyrene-HA, polyisobutylene-HA, PCL-HA, PLA-HA, PMMA-HA, PVDF-HA, SIS-heparin, polystyrene-heparin, polyisobutylene-heparin, PCL-heparin, PLA-heparin, PMMA-heparin, or PVDF-heparin.

As used herein, a conjugate is formed by combining one material, e.g., a polymer, with one or more other materials, e.g., a polymer of different nature, by ionic interaction, hydrogen bonding, or covalent bonding. The conjugate can be, for example, a block copolymer, an adduct, ion pair, polyelectrolyte complex, or chelate.

Active Agents

In accordance with a further embodiment of the invention, the composition described herein may optionally include one or more active agents. The active agent can be for inhibiting the activity of vascular smooth muscle cells. More specifically, the active agent can be aimed at inhibiting abnormal or inappropriate migration and/or proliferation of smooth muscle cells for the inhibition of restenosis.

The active agent can also include any substance capable of exerting a therapeutic, prophylactic or diagnostic effect. For example, the active agent can be for enhancing wound healing in a vascular site or improving the structural and elastic properties of the vascular site. Examples of active agents include antiproliferative substances such as actinomycin D, or derivatives and analogs thereof (manufactured by Sigma-Aldrich 1001 West Saint Paul Avenue, Milwaukee, Wis. 53233; or COSMEGEN available from Merck). Synonyms of actinomycin D include dactinomycin, actinomycin IV, actinomycin $I_1$, actinomycin $X_1$, and actinomycin $C_1$. The active agent can also fall under the genus of antineoplastic, anti-inflammatory, antiplatelet, anticoagulant, antifibrin, antithrombin, antimitotic, antibiotic, antiallergic and antioxidant substances.

Examples of such antineoplastics and/or antimitotics include paclitaxel (e.g. TAXOL® by Bristol-Myers Squibb Co., Stamford, Conn.), docetaxel (e.g. Taxotere, from Aventis S.A., Frankfurt, Germany) methotrexate, azathioprine, vincristine, vinblastine, fluorouracil, doxorubicin hydrochloride (e.g. Adriamycin® from Pharmacia & Upjohn, Peapack N.J.), and mitomycin (e.g. Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax ä (Biogen, Inc., Cambridge, Mass.). Examples of such cytostatic or antiproliferative agents include angiopeptin, angiotensin converting enzyme inhibitors such as captopril (e.g. Capoten® and Capozide® from Bristol-Myers Squibb Co., Stamford, Conn.), cilazapril or lisinopril (e.g. Prinivil® and Prinzide® from Merck & Co., Inc., Whitehouse Station, N.J.); calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents which may be appropriate include alpha-interferon, and genetically engineered epithelial cells. The foregoing substances are listed by way of example and are not meant to be limiting. Other active agents which are currently available or that may be developed in the future are equally applicable. Such other active agents include, for example, any anti-cancers, anti-genesis, antibiotics, anti-fungal agents and antibodies, proteins, peptides, anti-inflammatory agents, steroidal anti-inflammatory agents, antivirals, anticancer drugs, free radical scavengers, Everolimus, sirolimus, sirolimus derivatives, paclitaxel, estradiol, nitric oxide donors, super oxide dismutases, super oxide dismutases mimics, 4-amino-2,2,6, 6-tetramethylpiperidine-1-oxyl (4-amino-TEMPO), tacrolimus, dexamethasone, rapamycin, 40-O-(3-hydroxy)propyl-rapamycin, 40-O-[2-(2-hydroxy)ethoxy]ethyl-rapamycin, and 40-O-tetrazole-rapamycin, ABT-578, clobetasol, cytostatic agents, and a combination thereof.

The dosage or concentration of the active agent required to produce a favorable therapeutic effect should be less than the level at which the active agent produces toxic effects and greater than the minimum level at which therapeutic results are obtained. The dosage or concentration of the active agent required to inhibit the desired cellular activity of the vascular region can depend upon factors such as the particular circumstances of the patient; the nature of the trauma; the nature of the therapy desired; the time over which the administered ingredient resides at the vascular site; and if other active agents are employed, the nature and type of those agents or combinations of those agents. Therapeutic effective dosages can be determined empirically in vivo, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Examples of radiopaque elements include, but are not limited to, gold, tantalum, and platinum. An example of a radioactive isotope is $^{32}$P. Sufficient amounts of such substances may be dispersed in the composition such that the substances are not present in the composition as agglomerates or flocs.

Method of Coating a Device

The composition described herein can be coated on an implantable device such as a stent by spray coating or any other coating process available in the art. Generally, the coating involves dissolving or suspending the composition, or one or more components thereof, in a solvent or solvent mixture to form a solution, suspension, or dispersion of the composition or one or more components thereof, applying the solution or suspension to an implantable device, and removing the solvent or solvent mixture to form a coating or a layer of coating. Suspensions or dispersions of the composition described herein can be in the form of latex or emulsion of microparticles having a size between 1 nanometer and 100 microns, preferably between 1 nanometer and 10 microns. Heat and/or pressure treatment can be applied to any of the steps involved herein. In addition, if desirable, the coating described here can be subjected to further heat and/or pressure treatment. Some additional exemplary processes of coating an implantable device that may be used to form a coating on an implantable using the composition described herein are described in, for example, Lambert T L, et al. Circulation, 1994; 90: 1003-1011; Hwang C W, et al. Circulation, 2001; 104: 600-605; Van der Giessen W J, et al. Circulation, 1996; 94: 1690-1697; Lincoff A M, et al. J Am Coll Cardiol 1997; 29: 808-816; Grube E. et al, J American College Cardiology Meeting, Mar. 6, 2002, ACCIS2002, poster 1174-15; Grube E, et al, Circulation, 2003, 107: 1, 38-42; Bullesfeld L, et al. Z Kardiol, 2003, 92: 10, 825-832; and Tanabe K, et al. Circulation 2003, 107: 4, 559-64.

The composition can be coated onto the implantable device in the form of a single layer of coating or components of the composition can be coated onto the device in the form of separate layers of coating.

As used herein, the term "solvent" refers to a liquid substance or composition that is compatible with the polymer and is capable of dissolving or suspending the polymeric composition or one or more components thereof at a desired concentration. Representative examples of solvents include chloroform, acetone, water (buffered saline), dimethylsulfoxide (DMSO), propylene glycol monomethyl ether (PM,) isopropylalcohol (IPA), n-propyl alcohol, methanol, ethanol, tetrahydrofuran (THF), dimethylformamide (DMF), dimethyl acetamide (DMAC), benzene, toluene, xylene, hexane, cyclohexane, heptane, octane, nonane, decane, decalin, ethyl acetate, butyl acetate, isobutyl acetate, isopropyl acetate, butanol, diacetone alcohol, benzyl alcohol, 2-butanone, cyclohexanone, dioxane, methylene chloride, carbon tetrachloride, tetrachloroethylene, tetrachloro ethane, chlorobenzene, 1,1,1-trichloroethane, 1,1,2-trichloroethane, formamide, hexafluoroisopropanol, 1,1,1-trifluoroethanol, and hexamethyl phosphoramide and a combination thereof.

Examples of such implantable devices include self-expandable stents, balloon-expandable stents, stent-grafts, grafts (e.g., aortic grafts), artificial heart valves, cerebrospinal fluid shunts, pacemaker electrodes, and endocardial leads (e.g., FINELINE and ENDOTAK, available from Guidant Corporation, Santa Clara, Calif.). The underlying structure of the device can be of virtually any design. The device can be made of a metallic material or an alloy such as, but not limited to, cobalt chromium alloy (ELGILOY), stainless steel (316L), high nitrogen stainless steel, e.g., BIODUR 108, cobalt chrome alloy L-605, "MP35N," "MP20N," ELASTINITE (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from Standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. Devices made from bioabsorbable or biostable polymers could also be used with the embodiments of the present invention. In one embodiment, the implantable device is a stent.

The compositions described herein can be coated onto a bare metallic or polymeric implantable device or on top of a drug eluting coating on the implantable device.

Method of Use

In accordance with embodiments of the invention, a composition in the various embodiments as described above can be applied to an implantable device or prosthesis, e.g., a stent. For compositions including one or more active agents, the agent will remain on the medical device such as a stent during delivery and expansion of the device, and released at a desired rate and for a predetermined duration of time at the implantation site. Preferably, the medical device is a stent. A stent having the above-described coating is useful for a variety of medical procedures, including, by way of example, treatment of obstructions caused by tumors in bile ducts, esophagus, trachea/bronchi and other biological passageways. A stent having the above-described coating is particularly useful for treating occluded regions of blood vessels caused by atherosclerosis, or abnormal or inappropriate migration and proliferation of smooth muscle cells, thrombosis, and restenosis. Stents may be placed in a wide variety of blood vessels, both arteries and veins. Representative examples of sites include the iliac, renal, and coronary arteries.

The implantable device comprising a coating described herein can be used to treat an animal having a condition or disorder that requires a treatment. Such an animal can be treated by, for example, implanting a device described herein in the animal. Preferably, the animal is a human being. Exemplary disorders or conditions that can be treated by the method disclosed herein include, but not limited to, occlusive atherosclerotic lesions in the coronary vasculature, neointimal hyperplasia in the coronary arteries, restenosis in the coronary arteries, vulnerable plaques of the coronary arteries, atherosclerosis in the renal arteries, atherosclerosis in the carotid arteries, atherosclerosis in the neurovasculature, atherosclerosis in the iliac arteries, atherosclerosis in the femoral arteries, atherosclerosis in the popliteal arteries, atherothrombosis, and occlusive tumors of the prostate, liver, or gastrointestinal tract.

EXAMPLES

The embodiments of the present invention will be illustrated by the following set forth prophetic examples. All parameters and data are not to be construed to unduly limit the scope of the embodiments of the invention.

Example 1

The Polymer of Formula IV as a Topcoat in a Drug Eluting Stent Coating for the Controlled Release of Paclitaxel from a Stent A first composition is prepared by mixing the following components:
(a) 2.0 mass % of poly(n-butyl methacrylate) (PBMA), and
(b) the balance, a 50/50 blend by weight of acetone and cyclohexanone.

The first composition is applied onto the surface of bare 12 mm small VISION™ stent (available from Guidant Corporation). Coating is sprayed and dried to form a primer layer. A spray coater is used having a 0.014 round nozzle maintained at about body temperature with a feed pressure 2.5 psi (0.17 atm) and an atomization pressure of about 15 psi (1.02 atm). Coating is applied at 20 µg per pass, in between which the stent is dried for 10 seconds in a flowing air stream at 50 C. Approximately 110 µg of wet coating is applied. The stents are baked at 50 C for one hour, yielding a primer layer composed of approximately 100 µg of PBMA.

A drug reservoir layer is applied onto the primer layer, using the same spraying technique, equipment, and formulation used for the applying the primer. A second composition is prepared by mixing the following components:
(a) 2.0 mass % of the polymer of formula III,
(b) 0.67 mass % of paclitaxel, and
(c) the balance, a 50/50 blend of chloroform and 1,1,2-trichloroethane.

In this case approximately 220 µg of wet coating is applied, followed by drying, e.g., baking at 50 C for about one hour, yielding about 200 µg of drug-polymer reservoir layer. A polymer of the current invention is used as a topcoat layer. Starting with the same polymer of Formula III used in the drug reservoir, grafting of PEG is carried out using an amino-terminated mPEG of molecular weight of 3400 Daltons. Enough PEG derivative is conjugated so that the final composition is 20% by weight PEG. Using this composition, namely:
(a) 2.0 mass % of (IV) as described above, and
(b) the balance, a 50/50 blend of chloroform and 1,1,2-trichloroethane.

This composition can be applied onto the drug reservoir layer to form a topcoat layer. Using the same spraying technique and equipment used for applying the drug reservoir layer. Approximately 120 µg of wet topcoat is applied followed by baking at 50 C for one hour, yielding a 100 µg topcoat layer of Formula IV to act as a biobeneficial topcoat.

Example 2

The Polymer of Formula IV is Used as a Matrix in a Drug Eluting Stent Coating for the Controlled Release of Paclitaxel from a Stent A first composition is prepared by mixing the following components:
(a) 2.0 mass % of poly(n-butyl methacrylate) (PBMA), and
(b) the balance, a 50/50 blend by weight of acetone and cyclohexanone.

The first composition is applied onto the surface of bare 12 mm small VISION™ stent (available from Guidant Corporation). Coating is sprayed and dried to form a primer layer. A spray coater is used having a 0.014 round nozzle maintained at about body temperature with a feed pressure 2.5 psi (0.17 atm) and an atomization pressure of about 15 psi (1.02 atm). Coating is applied at 20 μg per pass, in between which the stent is dried for 10 seconds in a flowing air stream at 50 C. Approximately 110 μg of wet coating was applied. The stents are baked at 50 C for one hour, yielding a primer layer composed of approximately 100 μg of PBMA.

A drug reservoir layer is applied onto the primer layer, using the same spraying technique, equipment, and formulation used for the applying the primer. Starting with the same polymer of Formula III, grafting of PEG is carried out using an amino-terminated mPEG of molecular weight of 550 Daltons. Enough PEG derivative is conjugated so that the final composition is 5% by weight PEG. Using this composition, namely:

(a) 2.0 mass % of (IV) as described above,
(b) 0.5 mass % of paclitaxel, and
(c) the balance, a 50/50 blend of chloroform and 1,1,2-trichloroethane.

This composition can be applied onto the primer layer to form a drug reservoir layer. Using the same spraying technique and equipment used for applying the drug reservoir layer. Approximately 280 μg of wet is applied followed by baking at 50° C. for one hour, yielding a 250 μg reservoir layer of the polymer of Formula IV to act as a reservoir polymer with higher drug permeability than the polymer of formula III.

Example 3

The Polymer of Formula IV as a Topcoat in a Drug Eluting Stent Coating for the Controlled Release of Everolimus from a Stent A first composition is prepared by mixing the following components:

(a) 2.0 mass % of poly(ethylene-co-vinyl alcohol) (EVAL E-151A), and
(b) the balance, a 70/30 blend by weight of dimethylacetamide and tetrahydrofuran.

The first composition is applied onto the surface of bare 12 mm small VISION™ stent (available from Guidant Corporation). Coating is sprayed and dried to form a primer layer. A spray coater is used having a 0.014 round nozzle maintained at about body temperature with a feed pressure 2.5 psi (0.17 atm) and an atomization pressure of about 15 psi (1.02 atm). Coating is applied at 10 μg per pass, in between which the stent is dried for 10 seconds in a flowing air stream at 50 C. Approximately 120 μg of wet coating was applied. The stents are baked at 14° C. for one hour, yielding a primer layer composed of approximately 100 μg of EVAL. A drug reservoir layer is applied onto the primer layer, using the same spraying technique, equipment, and polymer as used in applying the primer:

(a) 2.0 mass % of EVAL E-151A as described above,
(b) 0.67 mass % of everolimus, and
(c) the balance, a 70/30 blend by weight of dimethylacetamide and tetrahydrofuran.

This composition can be applied onto the primer layer to form a drug reservoir layer. Using the same spraying technique and equipment used for applying the drug reservoir layer. Approximately 240 μg of wet is applied followed by baking at 80 C for 30 minutes, yielding a 223 μg reservoir layer. A polymer of the current invention is used as a topcoat layer. Starting with the same polymer of Formula III used in the drug reservoir, grafting of PEG is carried out using an amino-terminated mPEG of molecular weight of 500 Daltons. Enough PEG derivative is conjugated so that the final composition is 20% by weight PEG. Using this composition, namely:

(a) 2.0 mass % of (IV) as described above, and
(b) the balance, a 50/50 blend of chloroform and 1,1,2-trichloroethane This composition can be applied onto the drug reservoir layer to form a topcoat layer. Using the same spraying technique and equipment used for applying the drug reservoir layer. Approximately 120 μg of wet topcoat is applied followed by baking at 50 C for one hour, yielding a 100 μg topcoat layer of Formula IV to act as a biobeneficial topcoat.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A composition for coating an implantable device comprising a block copolymer conjugate having the structure:

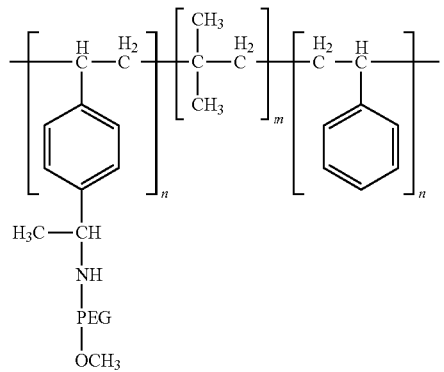

wherein m and n are positive integers;
or the structure

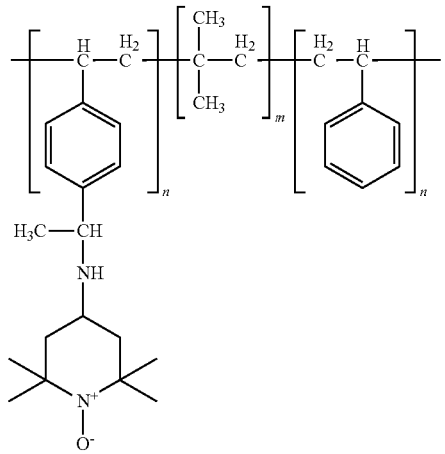

wherein m and n are positive integers.

2. The composition of claim 1, further comprising a bioactive agent.

3. The composition of claim 2, wherein the bioactive agent is selected from the group consisting of proteins, peptides, anti-inflammatory agents, antivirals, anticancer drugs, anticoagulant agents, free radical scavengers, and a combination thereof.

4. The composition of claim 3, wherein the bioactive agent is selected from the group consisting of everolimus, sirolimus, sirolimus derivatives, paclitaxel, estradiol, steroidal anti-inflammatory agents, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, 40-O-(3-hydroxy)propyl-rapamycin, 40-O-[2-(2-hydroxy)ethoxy]ethyl-rapamycin, and 40-O-tetrazole-rapamycin, ABT-578, clobetasol, cytostatic agents, and a combination thereof.

5. An implantable device comprising a coating which comprises a composition of claim 1.

6. The implantable device of claim 5, wherein the composition further comprising a bioactive agent.

7. The implantable device of claim 6, wherein the bioactive agent is selected from the group consisting of proteins, peptides, anti-inflammatory agents, antivirals, anticancer drugs, anticoagulant agents, and free radical scavengers.

8. The implantable device of claim 6, wherein the bioactive agent is selected from the group consisting of everolimus, sirolimus, sirolimus derivatives, paclitaxel, estradiol, steroidal anti-inflammatory agents, antibiotics, nitric oxide donors, super oxide dismutases, super oxide dismutases mimics, 4-amino-2,2,6,6-tetramethylpiperidine-1-oxyl (4-amino-TEMPO), tacrolimus, dexamethasone, rapamycin, 40-O-(3-hydroxy)propyl-rapamycin, 40-O-[2-(2-hydroxy)ethoxy]ethyl-rapamycin, and 40-O-tetrazole-rapamycin, ABT-578, clobetasol, cytostatic agents, and a combination thereof.

9. The implantable device of claim 5, which is a stent.

10. The implantable device of claim 9, which is a drug eluting stent (DES).

* * * * *